United States Patent
Georgeson

(10) Patent No.: US 7,712,369 B2
(45) Date of Patent: May 11, 2010

(54) ARRAY-BASED SYSTEM AND METHOD FOR INSPECTING A WORKPIECE WITH BACKSCATTERED ULTRASONIC SIGNALS

(75) Inventor: Gary E. Georgeson, Federal Way, WA (US)

(73) Assignee: The Boeing Company, Chicago, IL (US)

(*) Notice: Subject to any disclaimer, the term of this patent is extended or adjusted under 35 U.S.C. 154(b) by 0 days.

(21) Appl. No.: 11/945,735

(22) Filed: Nov. 27, 2007

(65) Prior Publication Data

US 2009/0133501 A1 May 28, 2009

(51) Int. Cl.
  *G01N 29/00* (2006.01)
(52) U.S. Cl. ............... 73/632; 73/602; 73/618; 73/620; 73/629
(58) Field of Classification Search ............ 73/632, 73/628, 633, 640, 641, 618, 620; 600/443, 600/444, 447
See application file for complete search history.

(56) References Cited

U.S. PATENT DOCUMENTS

| | | | |
|---|---|---|---|
| 3,402,598 A * | 9/1968 | Colgate ............... | 73/629 |
| 3,712,119 A | 1/1973 | Cross, et al. | |
| 4,058,003 A | 11/1977 | Macovski | |
| 4,487,070 A | 12/1984 | Gerling et al. | |
| 4,591,511 A | 5/1986 | Peebles, Jr. | |
| 4,596,145 A | 6/1986 | Smith et al. | |
| 4,869,109 A | 9/1989 | Miglianico et al. | |
| 4,873,984 A * | 10/1989 | Hunt et al. ............. | 600/443 |
| 4,881,177 A | 11/1989 | McClean et al. | |
| 4,881,549 A * | 11/1989 | Rhyne ................ | 600/443 |
| 5,005,420 A | 4/1991 | Miyajima | |
| 5,073,814 A | 12/1991 | Cole, Jr. et al. | |
| 5,091,893 A | 2/1992 | Smith et al. | |
| 5,165,270 A | 11/1992 | Sansalone et al. | |
| 5,390,544 A | 2/1995 | Madras | |
| 5,557,108 A * | 9/1996 | Tumer ............... | 250/390.04 |
| 5,614,670 A | 3/1997 | Nazarian et al. | |
| 5,680,863 A | 10/1997 | Hossack et al. | |
| 5,735,282 A | 4/1998 | Hossack | |
| 5,814,731 A | 9/1998 | Alexander et al. | |

(Continued)

FOREIGN PATENT DOCUMENTS

GB        1474932 A       5/1977

OTHER PUBLICATIONS

Y. Bar-Cohen, R.L. Crane, *Acoustic-Backscattering Imaging of Subcritical Flaws in Composites*, Materials Evaluation 40, 1982, pp. 970-975 (6 pages).

(Continued)

*Primary Examiner*—J M Saint Surin
(74) *Attorney, Agent, or Firm*—Alston & Bird LLP

(57) ABSTRACT

A method and an array-based system for inspecting a structure are provided that can identify unacceptable levels of porosity, microcracking or defects attributable to thermal damage. The inspection system includes a two-dimensional array of ultrasonic transducers, and an array controller configured to trigger at least one ultrasonic transducer to emit an ultrasonic signal into the structure. The array controller is also configured to receive data representative of backscattered signals preferentially received by at least one ultrasonic transducer from a portion of the structure offset from the at least one ultrasonic transducer that was triggered to emit the ultrasonic signal.

17 Claims, 7 Drawing Sheets

U.S. PATENT DOCUMENTS

| | | | |
|---|---|---|---|
| 5,983,701 | A | 11/1999 | Hassani et al. |
| 6,234,025 | B1 | 5/2001 | Gieske et al. |
| 6,424,597 | B1 | 7/2002 | Bolomey et al. |
| 6,428,477 | B1* | 8/2002 | Mason .................. 600/437 |
| 6,446,509 | B1 | 9/2002 | Takada et al. |
| 6,476,541 | B1 | 11/2002 | Smith et al. |
| 6,586,702 | B2 | 7/2003 | Wiener-Avnear et al. |
| 6,591,679 | B2 | 7/2003 | Kenefick et al. |
| 6,598,485 | B1 | 7/2003 | Lin et al. |
| 6,656,124 | B2 | 12/2003 | Flesch et al. |
| 6,666,825 | B2* | 12/2003 | Smith et al. .............. 600/459 |
| 6,681,466 | B2 | 1/2004 | David et al. |
| 6,691,576 | B1 | 2/2004 | Sato et al. |
| 6,736,779 | B1* | 5/2004 | Sano et al. .............. 600/447 |
| 6,777,931 | B1 | 8/2004 | Takada et al. |
| 6,798,717 | B2 | 9/2004 | Wiener-Avnear et al. |
| 6,822,374 | B1 | 11/2004 | Smith et al. |
| 6,910,380 | B2* | 6/2005 | Ogawa .................. 73/628 |
| 7,263,888 | B2* | 9/2007 | Barshinger et al. ............ 73/606 |
| 7,508,971 | B2* | 3/2009 | Vaccaro et al. ............. 382/141 |
| 2002/0128790 | A1 | 9/2002 | Woodmansee |
| 2004/0123665 | A1 | 7/2004 | Blodgett et al. |
| 2005/0132809 | A1 | 6/2005 | Fleming et al. |
| 2006/0004499 | A1 | 1/2006 | Trego et al. |
| 2006/0186260 | A1 | 8/2006 | Magnuson et al. |
| 2007/0051177 | A1 | 3/2007 | Gifford et al. |
| 2008/0229834 | A1* | 9/2008 | Bossi et al. ................. 73/627 |

OTHER PUBLICATIONS

Lewis T. Thomas III, Eric I. Madaras, J.G. Miller, *Two-Dimensional Imaging of Selected Ply Orientations In Quasi-Isotropic Composite Laminates Using Polar Backscattering*, Ultrasonics Symposium, 1982, pp. 965-970, 0090-5607/82/0000-0965 IEEE.

J. Qu, J.D. Achenbach, *Analytical Treatment of Polar Backscattering From Porous Composites*, Review of Progress in Quantitative Nondestructive Evaluation, 1987, pp. 1137-1146, vol. 6B, Plenum Press, New York, NY.

Ronald A. Roberts, *Porosity Characterization in Fiber-Reinforced Composites by Use of Ultrasonic Backscatter*, Review of Progress in Quantitative Nondestructive Evaluation, 1987, pp. 1147-1156, vol. 6B, Plenum Press, New York, NY.

S.M. Handley, M.S. Hughes, J.G. Miller, E.I. Madaras, *Characterization of Porosity in Graphite/Epoxy Composite Laminates With Polar Backscatter and Frequency Dependent Attenuation*, Ultrasonics Symposium, 1987, pp. 827-830, 0090-5607/87/0000-0827 IEEE.

J. Qu, J.D. Achenbach, *Backscatter From Porosity in Cross-Ply Composites*, Review of Progress in Quantitative Nondestructive Evaluation, 1988, pp. 1029-1036, vol. 7B, Plenum Press, New York, NY.

Ronald A. Roberts, *Characterization of Porosity in Continuous Fiber-Reinforced Composites With Ultrasonic Backscatter*, Review of Progress in Quantitative Nondestructive Evaluation, 1988, pp. 1053-1062, vol. 7B, Plenum Press, New York, NY.

T. Ohyoshi, J.D. Achenback, *Effect of Bottom-Surface Reflections on Backscatter From Porosity in a Composite Layer*, Review of Progress in Quantitative Nondestructive Evaluation, 1988, pp. 1045-1052, vol. 7B, Plenum Press, New York, NY.

Manohar Bashyam, *Ultrasonic NDE for Ceramic—And Metal—Matrix Composite Material Characterization*, Review of Progress in Quantitative Nondestructive Evaluation, 1991, pp. 1423-1430, vol. 10B, Plenum Press, New York, NY.

Daniel Grolemund, Chen S. Tsai, *Statistical Moments of Backscattered Ultrasound in Porous Fiber Reinforced Composites*, IEEE Transactions on Ultrasonics, Ferroelectrics, and Frequency Control, Mar. 1998, pp. 295-304, vol. 45, No. 2.

Jocelyn Langlois and R.S. Frankle, *Use of Flexible Ultrasonic Arrays in Inspection*, NDT.Net—Mar. 1999, vol. 4, No. 3, 5 pages.

F. Aymerich, S. Meili, *Ultrasonic Evaluation of Matrix Damage in Impacted Composite Laminates*, Composites Part B: Engineering, Jan. 2000, pp. 1-6, vol. 31, Issue 1, S359-8368(99) 00067-0.

*General Provisions For Boeing (Buyer) Purchase Contract to Seller (Seller) for Flexible Ultrasonic Array Demonstration Unit*, privately exchanged between Buyer and Seller on approximately Mar. 24, 2004, never published, redacted copy 6 pages.

Atul S. Ganpatye, *Ultrasonic Ply-by-ply Detection of Matrix Cracks in Laminated Composites*, 43$^{rd}$ AIAA Aerospace Sciences Meeting and Exhibit, American Institute of Aeronautics and Astronautics, Inc., Jan. 2005, pp. 1-9. Reno, Nevada.

*SonoFlex™ Flexible Ultrasonic Array Systems*, The Boeing Company, Seattle, WA, publicly available at the Aging Aircraft Conference in Atlanta, Mar. 7-9, 2006, 1 page.

*Flexible Ultrasonic Arrays, HD Laboratories, Inc., NDT and Electronic Engineers*; 2 pages, available at http://www.hdlabs.com/NDT/Flexible/Arrays/flexiblearrays.htm; Apr. 28, 2006; publicly available on or before Sep. 1, 2005; 2 pages.

International Search Report for PCT Application No. PCT/2008/057165 filed Mar. 14, 2008; Date of Completion: May 28, 2008; Date of Mailing: Jun. 4, 2008.

Written Opinion for PCT Application No. PCT/2008/057165 filed Mar. 14, 2008; Date of Completion: May 28, 2008; Date of Mailing: Jun. 4, 2008.

\* cited by examiner

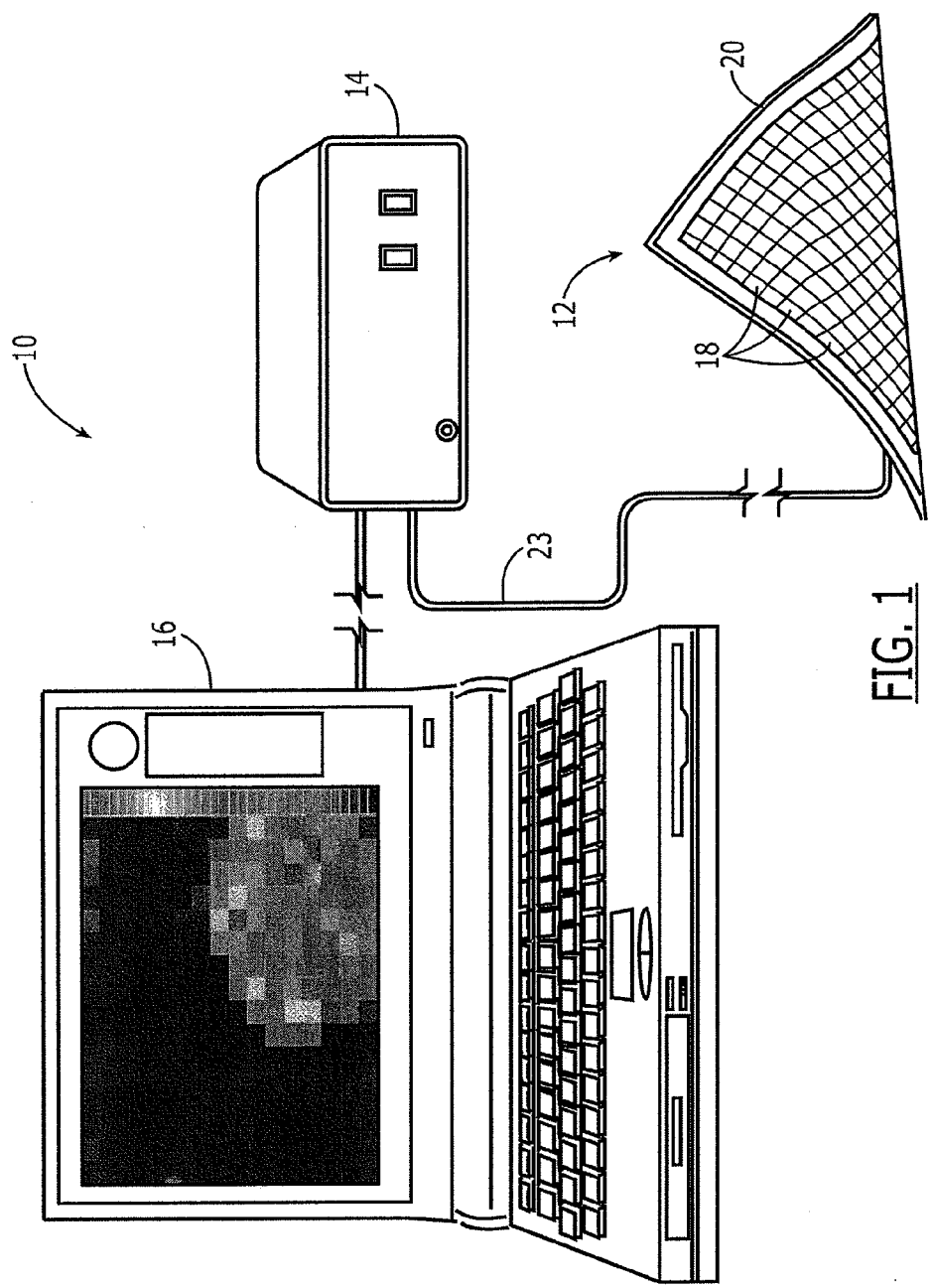

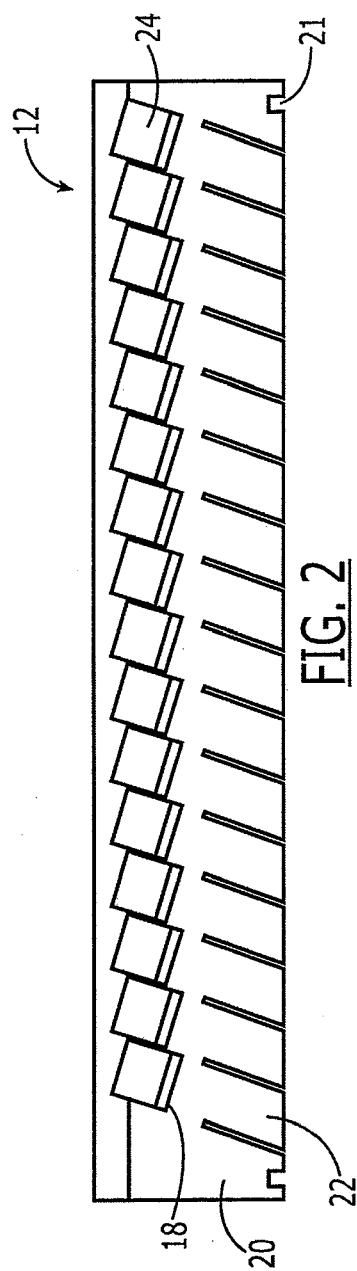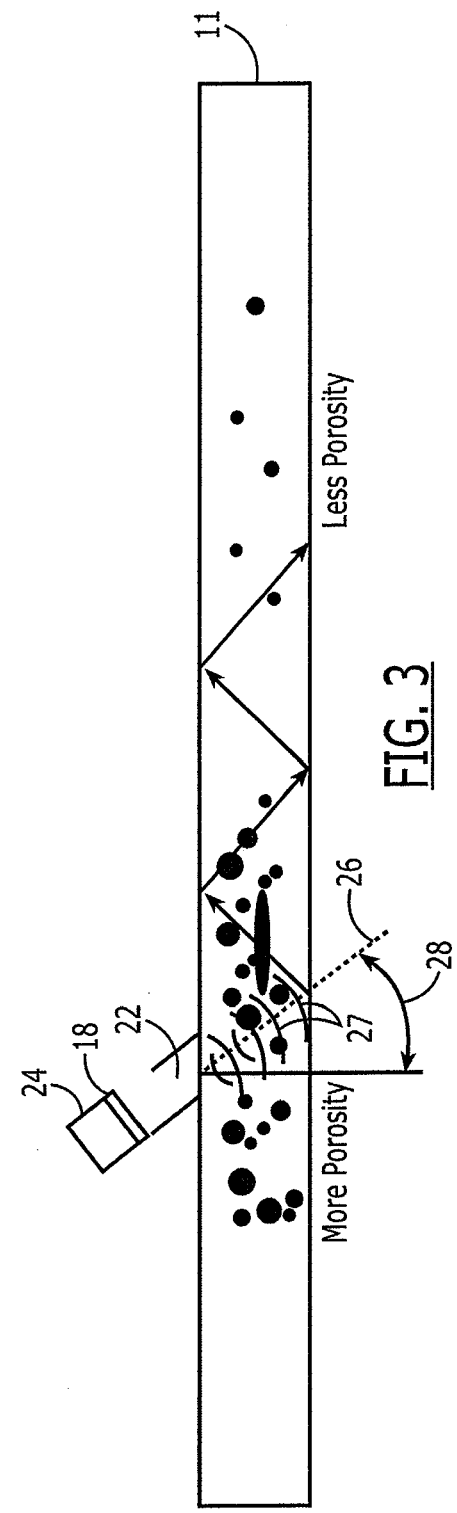

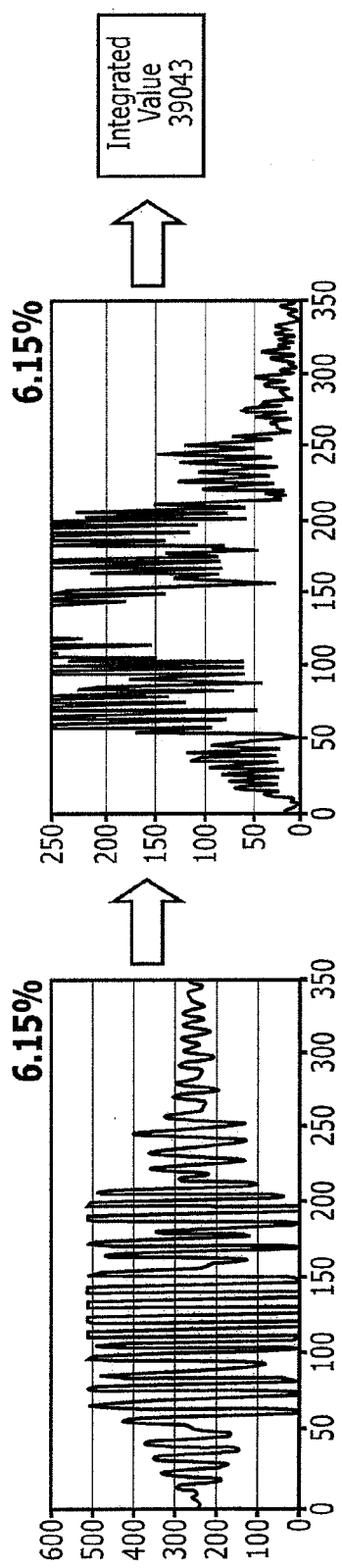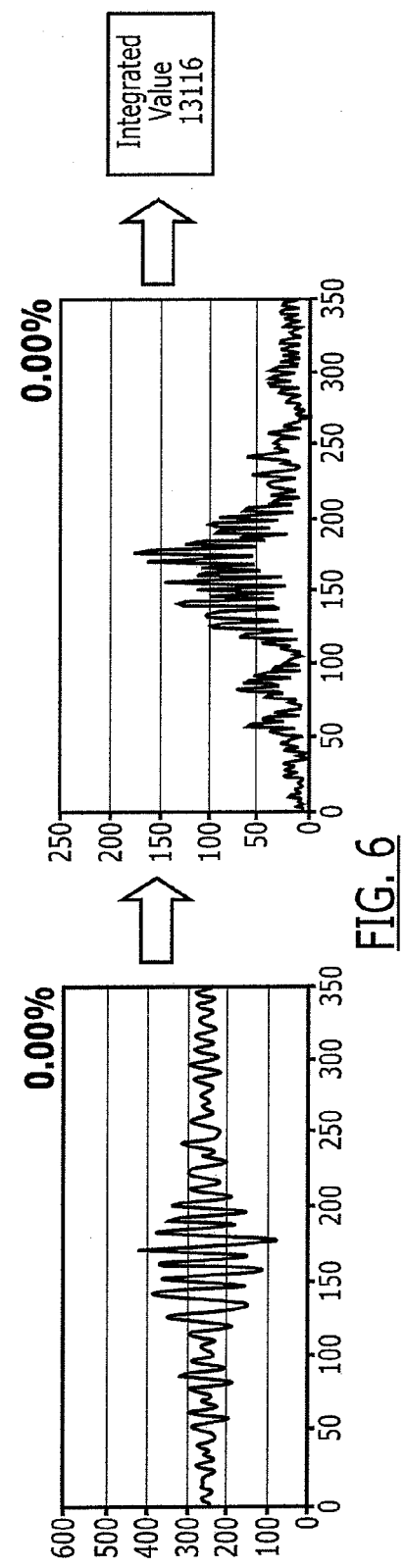
FIG. 5
FIG. 6

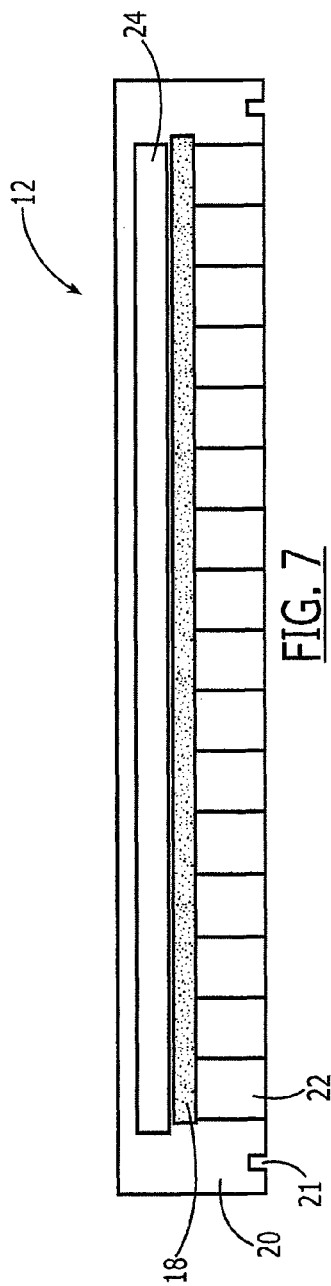
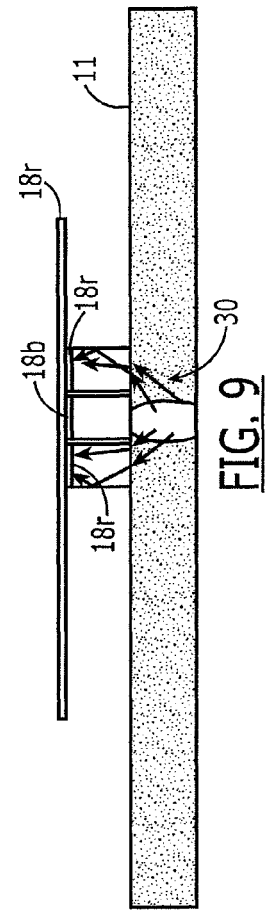
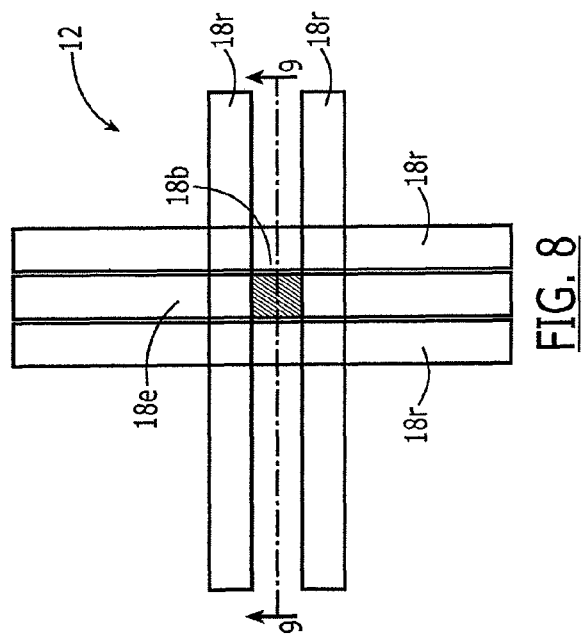

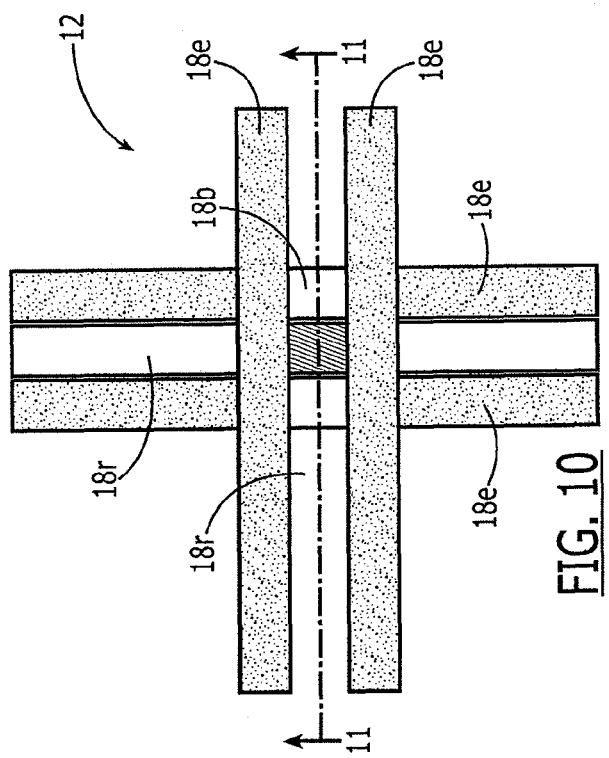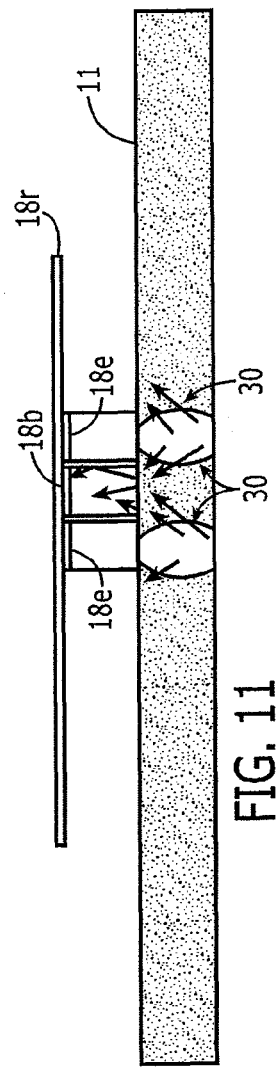

ARRAY-BASED SYSTEM AND METHOD FOR INSPECTING A WORKPIECE WITH BACKSCATTERED ULTRASONIC SIGNALS

TECHNICAL FIELD

Embodiments relate generally to a system and method for inspecting a structure and, more particularly, to an array-based system and method for detecting, for example, porosity, microcracks or thermal damage via a single-sided ultrasonic inspection of a structure.

BACKGROUND

Non-destructive inspection (NDI) of structures involves thoroughly examining a structure without harming the structure or requiring its significant disassembly. Non-destructive inspection is typically preferred to avoid the schedule, labor, and costs associated with removal of a part for inspection, as well as avoidance of the potential for damaging the structure. Non-destructive inspection is advantageous for many applications in which a thorough inspection of the exterior and/or interior of a structure is required. For example, non-destructive inspection is commonly used in the aircraft industry to inspect aircraft structures for any type of internal or external damage to or defects (flaws) in the structure. Inspection may be performed during manufacturing or after the completed structure has been put into service, including field testing, to validate the continued integrity and fitness of the structure.

During NDI, one or more sensors may move over the portion of the structure to be examined, and receive data regarding the structure. Various types of sensors may be used to perform non-destructive inspection. For example and without limitation, a pulse-echo (PE), through transmission (TT), or shear wave sensor may be used to obtain ultrasonic data, such as for thickness gauging, detection of laminar defects and/or crack detection in the structure.

In some circumstances, only a single surface of the structure may be accessible for inspection purposes, which may limit the potential inspection techniques. For example, in the field, access to interior surfaces of the structure may be restricted, requiring disassembly of the structure and introducing additional time and labor. Similarly, during manufacture, one of the surfaces may be disposed upon a mandrel and be inaccessible, at least without undesirable and time-consuming disassembly.

While single-sided inspection techniques, such as PE, can be employed to detect disbonds, delaminations, cracks or other substantial defects, it may be difficult to detect porosity in certain situations, such as situations in which the structure under inspection is ultrasonically coupled to another structure, such as a mandrel or other backing material, absent a TT inspection technique. In this regard, in PE, the amplitude of the reflection from the back surface, i.e., the surface opposite the inspection sensor, is used as a gage to determine the percent of porosity by comparing the reflection from the back surface of the structure under inspection with standard data gathered from prior inspections of reference samples of known porosity. Accordingly, porosity may be difficult to detect and/or quantify, especially in conjunction with structures that are only amenable of single-sided inspection and are ultrasonically coupled to another structure, since the ultrasonic coupling will reduce the reflection from the back surface by an unknown amount. Such difficulties in accurately detecting and/or quantifying porosity may be problematic in composite manufacturing processes in which it is desirable to monitor the quality of the composite material including, for example, the porosity of the composite material to insure that the manufacturing process is performing in the desired manner.

While it is generally desirable to detect porosity during or following manufacture, it is similarly desirable to be able to identify microcracking or thermal damage in the field or otherwise once the composite material has been placed in service. Microcracking can occur due to fatigue or thermal cycling of composites. Microcracks generally consist of multiple small cracks in the resin and fibers of a composite structure. Typical crack sizes are in the 0.010 inch to over 0.200 inch range. Thermal damage may be attributable to various sources and, in aerospace applications, may be attributable to engine exhaust impingement, overheated components in a confined space, or fires involving a component. Regardless of its source, thermal damage may degrade the matrix properties and the interface between matrix material and the embedded fibers, thereby leading to undesirable changes.

Conventionally, laboratory-based methods have been employed to detect and determine the extent of thermal damage. Unfortunately, the laboratory-based methods cannot generally be performed in the field and oftentimes require disassembly or other rework of the composite structure. As such, non-destructive methods of detecting thermal damage have been developed, including infrared (IR) spectroscopy, laser pumped florescence and high frequency eddy current inspection. However, IR spectroscopy and laser pumped fluorescence are generally localized techniques that may be capable of measuring thermal damage within one to three plies of the surface. For thicker structures, plies must generally be successively removed and then the remaining structure re-inspected to detect thermal damage deeper within a structure, thereby increasing the time and cost required for an inspection. High frequency eddy current inspection measures the change in resistance in the matrix material, such as that change in resistance attributable to overheating. However, high frequency eddy current inspection is also a near surface inspection method and generally cannot be utilized if the composite structure includes lightening strike protection. High frequency eddy current inspection may be also disadvantageously sensitive to conductive structures in the immediate vicinity of the inspection area and to the geometry of the structure.

Ultrasonic PE has also been employed in an effort to detect thermal damage. However, it may be difficult to detect thermal damage until the thermal damage is sufficiently substantial so as to result in discrete delaminations. Accordingly, thermal damage may be difficult to detect and/or quantify via ultrasonic PE at earlier stages.

In some instances, the thermal damage is not visible. Additionally, conventional nondestructive inspection techniques may not detect the thermal damage, particularly in instances in which the composite material must be inspected from a single side for at least the reasons described above in conjunction with porosity detection. Moreover, even in instances in which it is suspected that a composite structure has suffered thermal damage, such as a result of surface charring or discoloring, a portion of the composite structure may be removed and replaced. However, the removal and replacement may later prove to be completely unnecessary in instances in which the composite structure has, in fact, not been thermally damaged. Alternatively, the removal and replacement may later prove to be excessive in instances in which a larger portion of the composite structure is removed and replaced out of precaution than has been actually thermally damaged.

Additionally, while handheld inspection probes have been developed, it is sometimes desirable to inspect larger portions of a structure than those that can be quickly or efficiently inspected with a handheld probe. As such, robotic inspection scanners have been developed. However, robotic scanners can be somewhat expensive and may not be available in all locations, such as on the field or other remote locations, at which it is desirable to inspect a structure.

Thus, it would be desirable to be able to detect porosity, microcracking and/or thermal damage in an efficient manner, even in instances in which larger regions of a structure are to be inspected.

SUMMARY

A method and an array-based system for inspecting a workpiece are therefore provided that have embodiments that address at least some of the deficiencies identified with conventional techniques. In this regard, the method and system of at least some embodiments can identify unacceptable levels of porosity, microcracking or defects attributable to thermal damage, even in instances in which the workpiece can only be inspected from a single side. As such, the method and array-based system of at least some embodiments are suitable for inspection, either during manufacturing or once a workpiece has been placed in service in the field. Moreover, by utilizing an array of ultrasonic transducers, the system and method of at least some embodiments can inspect a workpiece in an efficient manner.

According to one aspect, a system is provided that includes a two-dimensional array of ultrasonic transducers configured to be disposed upon a surface of a structure. The system of this embodiment also includes an array controller configured to trigger at least one ultrasonic transducer to emit an ultrasonic signal into the structure. The array controller is also configured to receive data representative of backscattered signals preferentially received by at least one ultrasonic transducer from a portion of the structure offset from the at least one ultrasonic transducer that was triggered to emit the ultrasonic signal. In one embodiment, the two-dimensional array of ultrasonic transducers includes a plurality of ultrasonic transducers that are each positioned to emit ultrasonic signals that propagate along a predefined axis of propagation that intersects the surface of the structure at a non-orthogonal angle. In this embodiment, the array controller may be configured to trigger the same ultrasonic transducer(s) to both emit an ultrasonic signal into the structure and to receive the backscattered signals from the structure.

According to another embodiment, a system is provided that includes an array controller configured to trigger at least one first linear array of ultrasonic transducers to emit ultrasonic signals into the structure. The array controller of this embodiment is also configured to receive data representative of backscattered signals received by at least one second linear array of ultrasonic transducers. One of the first and second linear arrays of ultrasonic transducers includes a linear array of ultrasonic transducers extending in a first direction. However, the other of the first and second linear arrays of ultrasonic transducers includes at least a pair of the linear arrays of ultrasonic transducers that extend in different directions relative to one another. The system of this embodiment also includes a computing device configured to determine a material property of the structure based upon the data representative of the backscattered signals received by the at least one second linear array of ultrasonic transducers.

According to another aspect, a method is provided for determining a material property of the structure. The method initially triggers at least one first linear array of ultrasonic transducers to emit ultrasonic signals into the structure. The method also receives data representative of backscattered signals received by at least one second linear array of ultrasonic transducers. One of the at least one first and second linear arrays of ultrasonic transducers include a linear array of ultrasonic transducers extending in the first direction. The other of the at least one first and second linear arrays of ultrasonic transducers includes at least a pair of the linear arrays of ultrasonic transducers extending in different directions relative to one another. The method also determines a material property of the structure based upon the data representative of the backscattered signals received by the at least one second linear array of ultrasonic transducers.

In one embodiment, the at least one first linear array of ultrasonic transducers may include at least a pair of linear arrays extending in one direction and at least a pair of linear arrays extending in a different direction. In this embodiment, the at least one second linear array of ultrasonic transducers may extend between at least one pair of the first linear arrays. In this embodiment, the pairs of linear arrays may bound at least one ultrasonic transducer through which the at least one second linear array of ultrasonic transducers may extend.

In one embodiment, the at least one second linear array of ultrasonic transducers includes at least a pair of linear arrays extending in one direction and at least a pair of linear arrays extending in a different direction. In this regard, the at least one first linear array of ultrasonic transducers may extend between the at least one pair of the second linear array. In one embodiment, the pairs of linear arrays bound at least one ultrasonic element with the at least one first linear array of ultrasonic transducers extending through the at least one ultrasonic transducer that is bounded by the pairs of linear arrays.

By determining and then analyzing the backscattered signals, the porosity, microcracking and/or thermal damage at a particular location can be more accurately assessed and anomalies can be detected. By utilizing backscattered signals and, accordingly, permitting inspection from a single side of the workpiece, the method and apparatus of at least some embodiments do not require disassembly of the workpiece and, instead, permit inspection, while the workpiece remains upon a mandrel or other tooling, such as during manufacture, or remains in an assembled form, such as while in the field or otherwise in service.

BRIEF DESCRIPTION OF THE SEVERAL VIEWS OF THE DRAWING(S)

Having thus described certain embodiments in general terms, reference will now be made to the accompanying drawings, which are not necessarily drawn to scale, and wherein:

FIG. 1 is a perspective view of an ultrasonic inspection system in accordance with one embodiment;

FIG. 2 is a side view of a two-dimensional array of an ultrasonic inspection system in accordance with one embodiment;

FIG. 3 is a schematic representation of the orientation of an ultrasonic transducer relative to a structure in accordance with one embodiment;

Figure 4A:
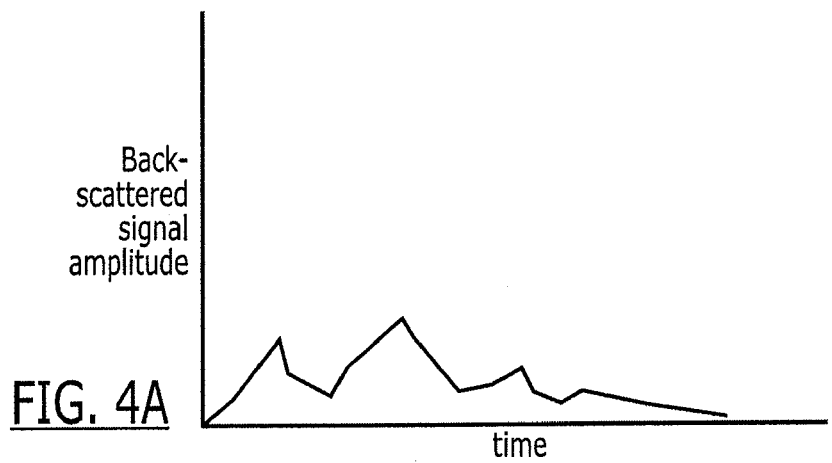
Figure 4B:
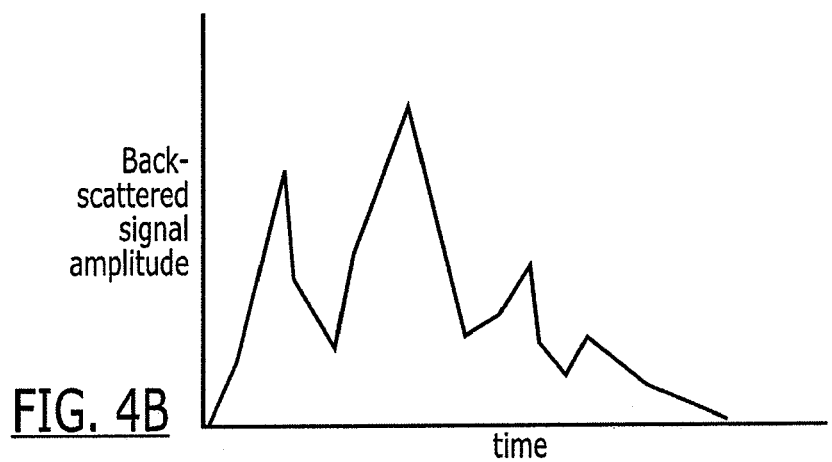
Figure 12:
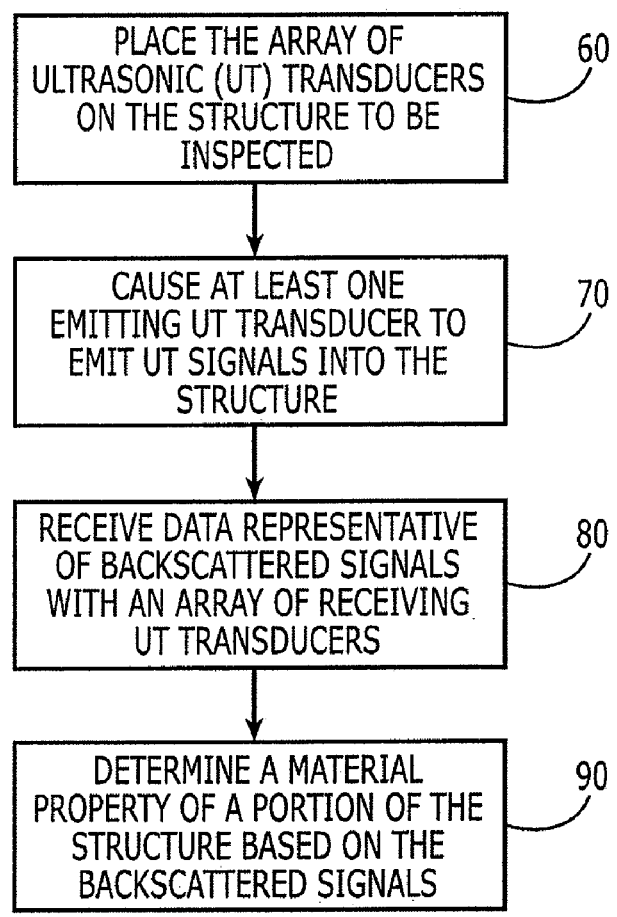

FIG. 4A graphically represents the signals received by an ultrasonic transducer during the inspection of a structure with little porosity, few microcracks and little heat damage in accordance with one embodiment;

FIG. 4B graphically represents the signals received by an ultrasonic transducer during the inspection of a structure with more substantial porosity, more microcracks and/or more substantial heat damage in accordance with one embodiment;

FIG. 5 graphically depicts the digitization, rectification and summation of the signals received by an ultrasonic transducer during the inspection of a structure with more substantial porosity, more microcracks and/or more substantial heat damage in accordance with one embodiment;

FIG. 6 graphically depicts the digitization, rectification and summation of the signals received by an ultrasonic transducer during the inspection of a structure with little porosity, few microcracks and little heat damage in accordance with one embodiment;

FIG. 7 is a side view of a two-dimensional array of an ultrasonic inspection system in accordance with another embodiment;

FIG. 8 is a schematic representation of several rows and columns of a two-dimensional array which depicts the positional relationship of the rows and columns of ultrasonic transducers that transmit and receive ultrasonic signals in accordance with one embodiment;

FIG. 9 is a schematic side view of the portion of the two-dimensional array of FIG. 8 taken along line 9-9 which illustrates the back scattering of the ultrasonic signals in response to porosity, microcracking or thermal damage in accordance with one embodiment;

FIG. 10 is a schematic representation of several rows and columns of a two-dimensional array which depicts the positional relationship of the rows and columns of ultrasonic transducers that transmit and receive ultrasonic signals in accordance with another embodiment;

FIG. 11 is a is a schematic side view of the portion of the two-dimensional array of FIG. 10 taken along line 11-11 which illustrates the back scattering of the ultrasonic signals in response to porosity, microcracking or thermal damage in accordance with another embodiment; and FIG. 12 is a flowchart of operations performed in accordance with one embodiment of the present disclosure.

DETAILED DESCRIPTION

Certain aspects of the disclosure now will be described more fully hereinafter with reference to the accompanying drawings, in which some, but not all embodiments of the inventions are shown. Indeed, these aspects may be embodied in many different forms and should not be construed as limited to the embodiments set forth herein; rather, these embodiments are provided so that this disclosure will satisfy applicable legal requirements. Like numbers refer to like elements throughout.

An ultrasonic inspection system 10 by which a structure may be inspected according to at least one embodiment is shown in FIG. 1. The ultrasonic inspection system 10 includes a two-dimensional array 12, an array controller 14, and a computing device 16. The ultrasonic inspection system can inspect a variety of structures formed of various materials. Structures that may be inspected with an embodiment of an inspection system may include, but are not limited to, composites such as carbon fiber or graphite reinforced epoxy (Gr/Ep) composites or foam filled composites, non-ferromagnetic metals (e.g. aluminum alloy, titanium alloy, or aluminum or titanium hybrid laminates such as GLARE or Ti/Gr), ferromagnetic metals, plastics, ceramics, polymers and virtually all solids, semi-solids and even liquids. A structure being inspected may be any myriad of shapes and/or sizes and used in a variety of applications, including aircraft, marine vehicles, automobiles, spacecraft and the like, as well as buildings. For example, the structure may be a foam filled hat stiffener or hat stringer. Moreover, the structure may be inspected prior to assembly, such as for porosity, or following assembly, such as for microcracking and/or thermal damage, as described below.

The ultrasonic inspection system 10 is generally configured for single-sided inspection of the workpiece as a result of its reliance upon backscattered signals. As such, the ultrasonic inspection apparatus is operable to inspect structures in instances in which the opposite side of the structure is inaccessible. For example, the ultrasonic inspection system is operable to inspect structures during manufacture in instances in which the structure is supported upon a mandrel or other tooling with the opposite or back side of the structure facing the mandrel or other tooling. Similarly, the ultrasonic inspection apparatus is operable to inspect structures following deployment even if only a single side is accessible, thereby potentially reducing instances in which the structure must be disassembled and/or removed from the field for inspection.

The two-dimensional array 12 may be flexible sensor array that includes ultrasonic sensors 18 bonded to a flexible mat 20 in a regularly spaced pattern. In one embodiment, each ultrasonic sensor includes a transducer element that is operable as a pulse-echo inspection sensor that both sends and receives ultrasonic waves. The transducer elements can be fabricated, for example and as known, from a polymer-based piezoelectric material called polyvinylidene fluoride (PVDF).

The periphery of the flexible mat 20 may define a gasket or groove 21, as shown in FIG. 2, for contacting an inspected structure and temporarily adhering the flexible sensor array to the structure when intervening air is removed by an optional vacuum system accessory of the ultrasonic inspection system 10. Alternatively, the flexible mat can be taped or otherwise temporarily adhered to an inspected structure by an adhesive material. Additionally, the flexible mat can be held in place by any suitable means, such as, without limitation, by hand, by a clamp or bracket or the like.

The sensor array 12 is illustrated in FIG. 1 to include two hundred and fifty six sensors disposed in rows and columns regularly spaced by one quarter of one inch to define a square grid pattern that is four inches wide on each side thereof. It should be understood that these descriptions relate nonetheless to sensor arrays having other numbers of sensors, other disposition patterns, and other pattern spacings. For example, these descriptions relate as well to a sensor array having one thousand and twenty fours sensors arranged in rows and columns regularly spaced by one quarter of one inch to define a square grid pattern that is eight inches wide on each side thereof. For further example these descriptions relate to sensor arrays defining hexagonal patterns and other patterns. Thus, these descriptions relate to a sensor array having any number of sensors arranged in any two-dimensional pattern.

The sensor array 12 may also include a plurality of segmented delay lines 22, as shown in FIG. 2 which depicts one exemplary linear array, e.g., one row or column, from the sensor array. In this regard, the sensor array and, more particularly, the flexible mat 20, may include a rubber pad positioned between the ultrasonic transducers 18 and the structure. The rubber pad may be divided into a plurality of segments with each segment being associated with and positioned in alignment with a respective ultrasonic transducer. As such, the segmented pad serves to at least partially isolate the ultrasonic signals transmitted and received by each ultrasonic transducer from those transmitted and received by the other ultrasonic transducers. As also shown in FIG. 2, the sensor array may include an acoustic backing material 24, such as epoxy resin containing high "Z" metal powder, positioned proximate to, but on the opposite side of the ultrasonic transducers from the structure that is to be inspected, thereby further directing the signals emitted by the ultrasonic transducers toward the structure or, at least, reducing the ultrasonic signals emitted by the ultrasonic transducers that propagate in a direction away from the structure. Other conventional acoustic backing materials include a soft encapsulent, such as epoxy resin, containing tungsten which serves as an acoustic absorber. A low melting point alloy, such as InPb, and one or more powders having high impedance characteristics, e.g., tungsten and copper, may also be used as an acoustic backing material. Depending upon the application and inspection environment, a couplant, such as an ultrasonic gel or water, may also be applied between the sensor array and the surface of the structure to provide a good path from the transducer into the structure.

The sensor array 12 is disposed in electronic communication with the array controller 14, for example by way of a cable 23 that can include any number of electrically conductive wires or by way of a wireless communications link. The array controller generally energizes each ultrasonic sensor 18 to send an ultrasonic pulse into an inspected structure and then receives data, typically in the form of an electrical signal, generated by the sensor when an ultrasonic echo signal returns from the structure.

The computing device 16, such as a personal computer, workstation or the like, receives the data from the array controller 14 and may process, store and/or graphically display the data for interpretation by a user in order to, for example, identifying damages in an inspected structure. The display of the data by the computing and display device may be provided in various forms. For example, the computing device of FIG. 1 provides a C-scan image. However, the computing device may display the data as an A-scan, a B-scan, or in other manners, if so desired.

In one embodiment depicted in FIG. 3 in which a single transducer 18 is shown for purposes of illustration, each transducer is oriented in such a manner as to introduce ultrasonic signals that propagate along an axis 26 positioned at an offset angle 28 relative to a predefined reference direction oriented normal to the surface of the structure that faces the inspection apparatus. The offset angle may have various predefined values, but is typically an acute, non-zero angle, such as between 5° and 45° and, in one embodiment, between 5° and 15° relative to the predefined reference direction. The ultrasonic transducer may emit ultrasonic signals at any of a plurality of different frequencies. Typically, the frequency of the ultrasonic signals varies in an inverse relationship to the thickness of the workpiece to be inspected. For example and without limitation, the ultrasonic transducer may transmit signals having a frequency of 10 MHZ for the inspection of thinner structures and a frequency of either 2.25 MHZ or 3.5 MHZ for the inspection of thicker structures. In one embodiment, however, the ultrasonic transducer emits signals having a frequency of 5 MHZ.

In operation, the sensor array 12 is positioned relative to the workpiece at a predefined location. The array controller 14 then actuates one or more ultrasonic transducers 18 to transmit an ultrasonic signal into the workpiece. Although the array controller can actuate the ultrasonic transducer in various manners, the array transducer of one embodiment includes an ultrasonic pulser receiver module or card for actuating the ultrasonic transducer(s). As described, the ultrasonic signals transmitted by the transducer propagate along an axis 26 that is disposed at an offset angle 28 from a normal to the surface of the workpiece. Upon encountering defects, such as porosity, a microcrack or thermal damage, a portion of the ultrasonic signals are backscattered as shown by the arcuate lines 27 of FIG. 3, and at least a portion of the backscattered signals are received and detected by the ultrasonic transducer. A large defect, such as a delamination, a disbond or the like, will not tend to scatter the signals, but will reflect the signals away from the transducer because of the angle. The backscattered signals attributable to the interaction of the ultrasonic signals with any single pore, microcrack or any single void or other defect created by, for instance, thermal impingement may be generally relatively small, but measurable. In order to evaluate the porosity, microcracking or the thermal damage of the workpiece at the respective location, the sum of the backscattered signals attributable to a plurality of the pores, a plurality of microcracks or a plurality of other defects at the respective locations, such as all of the pores, microcracks or all other defects in the beam path, may be determined. In this regard, the sum of the backscattered signals is informative since it may be only in the aggregate that the effects of porosity or microcracking or of the defects attributable to thermal damage upon the structure in that location can generally be assessed.

In this regard, the array controller 14 generally receives the output from the ultrasonic transducer(s) 18 over a predefined period of time with the output of the ultrasonic transducer(s) being representative of the amplitude of the signals received by the ultrasonic transducer(s) over the predetermined period of time. The array controller, in turn, provides data representative of the output of the ultrasonic transducer(s) to the computing device 16. In one embodiment, the computing device includes a digitizer for converting analog signals provided by the ultrasonic transducer(s) to corresponding digital signals. Additionally, the computing device can include a rectifier for rectifying the signals produced by the ultrasonic transducer(s) either prior to or following analog-to-digital conversion. As shown in FIG. 4A, the digitized and rectified signals representative of the amplitude of the backscattered signals received by an ultrasonic transducer are smaller when a structure having little porosity, few microcracks and little other damage is suspected. Alternatively, the digitized and rectified signals representative of the amplitude of the backscattered signals received by the ultrasonic transducer are larger over time when the structure has more substantial porosity, more microcracks or has suffered heat damage as shown in FIG. 4B.

By integrating or summing the signals, e.g., once digitized and rectified, representative of the amplitude of the backscattered signals received by the ultrasonic transducers 18 over a predetermined period of time, the computing device 16 can determine a measure representative of the degree of porosity, microcracking or thermal damage of the structure at the respective location. The computing device can then compare the sum of the backscattered signals received by the ultrasonic transducer with a predefined threshold, and the computing device can provide an indication of whether the structure at the respective location has an unacceptable degree of porosity, an unacceptable amount of microcracking or an unacceptable amount of thermal damage based upon the relationship of the sum of the backscattered signals received by the ultrasonic transducer to the predefined threshold. Typically, the predefined threshold is set to a value such that the sum of the backscattered signals received by the ultrasonic transducer over the predefined period at any location is indicative of an unacceptable level of porosity, microcracking or thermal damage if the sum exceeds a predefined threshold. Conversely, if the sum of the backscattered signals received by the ultrasonic transducer is less than the predefined threshold, the structure will generally be found to have acceptable levels of porosity, microcracking and thermal damage at the respective location. The value of the predefined threshold may vary, depending upon the application, the loads that are anticipated to be placed upon the structure and the tolerance of the structure and/or the application to the structural changes occasioned by porosity, microcracking or thermal damage, among other factors.

Although the predefined threshold may be defined in various manners, the predefined threshold may be determined by inspecting several samples constructed of the same materials and having the same thickness and configuration as the structure, but having different known levels of porosity, microcracking and/or thermal damage—some of which being known to be acceptable and others of which being known to be unacceptable. By comparing the measure representative of the degree of porosity, microcracking or thermal damage for each of the samples and determining those measures that are reflective of acceptable samples and those reflective of unacceptable samples, the threshold representative of the dividing line between acceptable and unacceptable levels of porosity, microcracking or thermal damage may be predefined.

The predetermined time period over which the backscattered signals received by the ultrasonic transducer 18 are summed generally corresponds to the thickness of the structure or, at least, the thickness of the portion of the structure that is desirably inspected. In this regard, the predetermined time period is generally set to equal or slightly exceed the time required for ultrasonic signals to propagate through the structure or at least that portion of the structure that is desired to be inspected and to then return to the ultrasonic transducer. While the predetermined time period can have a wide range of values depending upon the thickness of the structure or at least the thickness of that portion of the structure that is desirably inspected, the predetermined time period is typically one to a few microseconds.

By way of example, the leftmost graphs in FIGS. 5 and 6 illustrate the digitized output of an ultrasonic transducer 18 in terms of the relative ultrasonic amplitude of the backscattered signals over a period of 350 microseconds during the inspection of structures having a porosity of 6.15% and 0%, respectively. The relative ultrasonic amplitude of the backscattered signals represent the voltage produced by the ultrasonic transducer (E.G., piezoelectric transducer as the ultrasonic (stress) waves impinge upon the face of the transducer. The relative ultrasonic amplitude is typically measured in digitizer units with the actual voltage being unimportant so long as no changes are made to the ultrasonic transducer during a test. In turn, the rightmost graphs of FIGS. 5 and 6 depict the same output following rectification. By integrating the area under the respective graphs, a measure of 39,043 is obtained for the structure having a porosity of 6.15% and a measure of 13,116 is obtained for the structure having a porosity of 0%. As such, FIGS. 5 and 6 graphically illustrate the relationship between the area under the curve and the porosity (or likewise, microcracking or thermal damage) of a structure.

While the summation of the amplitudes of the backscattered signals received by the ultrasonic transducer 18 over a predetermined period of time permits the aggregate effect of pores, microcracks or defects to be determined in instances in which the effect of a single pore (or a small number of pores), a single microcrack (or a small number of microcracks) or a single defect (or a small number of defects) would otherwise be insignificant, the reliance predominantly upon backscattered signals, such as a result of the propagation of the ultrasonic signals at an offset angle relative to the normal to the surface of the structure as provided by the embodiment of FIG. 2, also advantageously permits the ultrasonic inspection system to obtain reliable results indicative of the porosity, microcracking or other damage of the structure. In terms of the embodiment of FIGS. 2 and 3, reflections from the front surface or back surface of the structure or from larger delaminations or disbonds within the structure cause a portion of the ultrasonic signals to be reflected. As a result of the propagation of the ultrasonic signals of this embodiment at the offset angle relative to the normal to the surface of the structure, the reflections of the ultrasonic signals do not return to the transducer, but are reflected at an angle based upon Snell's Law as schematically represented by FIG. 3. By avoiding the reflection of the ultrasonic signals from the front and back surfaces of the structure or from delaminations or disbonds from being detected by the ultrasonic transducer, the backscattered signals received by the ultrasonic transducer are not washed out or otherwise rendered insignificant as a result of the receipt of reflected signals having a larger, sometimes much larger, amplitude.

In the embodiment depicted in FIG. 2, the sensor array 12 includes a plurality of ultrasonic transducers 18 positioned so as to transmit signals at an offset angle 28 relative to the surface of the structure to be inspected. The array controller 14 may trigger the ultrasonic transducers of the sensor array in various manners. For example, the array controller can trigger individual ultrasonic transducers such that a first ultrasonic transducer emits an ultrasonic signal and receives any resulting backscattered signals from the structure. This process may then be repeated for each or at least a plurality of the ultrasonic transducers of the sensor array. Alternatively, the array controller can simultaneously trigger a plurality of ultrasonic transducers, such as a linear array, e.g., a row or a column, of ultrasonic transducers, to emit ultrasonic signals. The array controller of this embodiment can also cause a plurality of ultrasonic transducers, such as another linear array of ultrasonic transducers extending in a different direction, to receive the return signals from the structure. For example, the array controller may cause a row of ultrasonic transducers to emit ultrasonic signals and a column of ultrasonic signals to receive the return signals from the structure. Of the return signals received by the ultrasonic transducers, the return signals received by the ultrasonic transducer that is at the point of intersection of the linear arrays of ultrasonic transducers that were driven to emit and receive signals will be representative of the porosity, microcracks or damage of the structure proximate to, such as underlying, the respective transducer element, with the return signals received by the other ultrasonic transducers generally being of less relevance and, in many embodiments, simply ignored. For a sensor array having ultrasonic transducers arranged in a plurality of rows and columns, a row of ultrasonic transducers may be driven to emit ultrasonic signals with the columns of the sensor array being sequentially enabled to receive return signals in order to individually evaluate the backscattered signals received by each ultrasonic transducer of the respective row. This process can then be repeated for a plurality of rows, such as each row, as a sensor array. As such, the ultrasonic inspection system of this embodiment can individually evaluate the porosity, microcracking and/or damage of the structure proximate to, such as underlying, each ultrasonic transducer of the sensor array.

In another embodiment, the sensor array 12 includes a plurality of ultrasonic transducers 18, but the ultrasonic transducers are positioned so as to emit ultrasonic signals that propagate in a direction generally orthogonal to the surface of the structure to be inspected. For example, FIG. 7 depicts one linear array of ultrasonic transducers, e.g., one row or column, configured in accordance with this other embodiment.

Although the ultrasonic transducers are positioned to emit ultrasonic signals in a direction generally orthogonal to the surface of the structure, the ultrasonic transducers can be driven in such a manner as to preferentially detect backscattered signals. In this regard, the array controller 14 can trigger one or more ultrasonic transducers to emit ultrasonic signals. The array controller can then direct one or more ultrasonic transducers to receive the return signals from the structure. However, the array controller is configured such that the ultrasonic transducers that are directed to receive the return signals are different than, but proximate to, the ultrasonic transducers that are triggered to emit ultrasonic signals.

For example, the array controller 14 may direct that a single ultrasonic transducer 18 (i.e., an emitting transducer) emit ultrasonic signals into the structure. The array controller of this embodiment may then direct that one or more ultrasonic transducers (i.e., receiving transducers) that are different than, but adjacent to the emitting transducer receive the return signals occasioned as a result of the transmission of ultrasonic signals by the emitting transducer. As a result of the difference in position of the receiving transducers from the emitting transducer, the return signals received by the ultrasonic transducers generally include backscattered signals, such as those signals backscattered from porosity, microcracking or damage at a location proximate to, such as underlying, the emitting transducer.

While the array controller 14 may direct such emission and reception on an individual transducer basis, the array controller of one embodiment directs that linear arrays of ultrasonic transducers 18, such as rows or columns of ultrasonic transducers, be directed to transmit or receive. As shown in FIG. 8, the array controller may trigger a first linear array of ultrasonic transducers (i.e., an emitting array 18e), such as a first column of ultrasonic transducers, to emit ultrasonic signals into the structure. The array controller of this embodiment may also direct a pair of linear arrays of ultrasonic transducers (i.e., receiving arrays 18r) that extend in different directions from one another, such as a row and a column of ultrasonic transducers, to receive return signals from the structure. In the illustrated embodiment, for example, the array controller directs at least two columns of ultrasonic transducers and at least two rows of ultrasonic transducers to receive return signals from the structure. The receiving arrays are generally spaced from one another with the emitting arrays being positioned between a pair of the receiving arrays.

In the illustrated embodiment, for example, the rows and columns of ultrasonic transducers that are directed to receive the return signals, i.e., the receiving arrays 18r, bound or surround one or more ultrasonic transducers 18b. As also depicted by the illustrated embodiment, the column of ultrasonic transducers that is triggered to emit ultrasonic signals, i.e., the emitting array 18e, therefore includes the ultrasonic transducer that is bounded by those rows and columns of ultrasonic transducers that are directed to receive the return signal. As such, the return signals received by the rows and columns of ultrasonic transducers that bound the ultrasonic transducer are generally considered to receive backscattered signals that are representative of the porosity, microcracking or thermal damage proximate to, such as underlying, the ultrasonic transducer that is bounded. In this regard, FIG. 9 schematically depicts a manner in which some of the ultrasonic signals emitted by a respective ultrasonic transducer are backscattered (as shown by reference number 30) to adjacent ultrasonic transducers.

In still another embodiment, the array controller 14 of FIG. 1 may trigger two or more linear arrays of ultrasonic transducers (i.e., emitting arrays 18e) that extend in different directions, such as a row and a column of ultrasonic transducers, to concurrently emit ultrasonic signals. In the embodiment illustrated in FIG. 10, for example, the array controller directs that a pair of columns of ultrasonic transducers and a pair of rows of ultrasonic transducers simultaneously transmit ultrasonic signals into the structure. The array controller of this embodiment also directs at least one and, in the illustrated embodiment, a pair of linear arrays of ultrasonic transducers (i.e., receiving arrays 18r) such as a row and a column of ultrasonic transducers, to receive the return signals from the structure. In instances in which the emitting arrays are spaced apart from one another, the receiving array(s) may be positioned therebetween. In an analogous manner to that described above, the emitting arrays may bound, or surround, one or more ultrasonic transducers 18b. In this embodiment, each receiving array may include the ultrasonic transducer that is bounded. As a result, the return signals received by the receiving arrays will be indicative of the porosity, microcracking or thermal damage proximate to, such as underlying, the ultrasonic transducer that is bounded as a result of the back scattering of the ultrasonic signals 30 as shown in FIG. 11.

By thereafter repeating the foregoing process with respect to different combinations of the rows and columns of ultrasonic transducers 18 which bound different ultrasonic transducers 18b, the porosity, microcracking or thermal damage of the structure that underlie each of a plurality of ultrasonic transducers may be determined.

As described above, the results of the inspection can be processed in many different manners. For example, the sum of the amplitude of the backscattered signals within a predefined period of time at each respective location can be stored and/or analyzed to identify location(s) which would appear to have an undesirable amount of porosity, microcracking or thermal damage. In this regard, the array controller 14 can transmit the data, such as in either a wireline or wireless manner, to the computing device 16 for subsequent analysis, such as to identify location(s) which would appear to have an undesirable amount of porosity, microcracking or thermal damage. For example, by comparing the sum of the amplitude of the backscattered signals received by the ultrasonic transducer over a predetermined period of time at each location, the computing device can provide a warning, an alarm or the like to the operator of the inspection apparatus during the course of the inspection of any location(s) that appear to have an unacceptable degree of porosity, microcracking or thermal damage. Moreover, the results can be presented in a variety of manners, including in a numerical format representative of the sum of the amplitudes of the backscattered signals over a predetermined period of time at the different locations or graphically in which the sums of the amplitudes of the backscattered signals at each location are graphically depicted.

As noted above, the ultrasonic inspection system 10 can be deployed for various applications, including the inspection of a structure 12 during manufacture, in which case the ultrasonic inspection apparatus would generally inspect the structure for porosity, or following placement of the structure into service in the field, in which instances the ultrasonic inspection apparatus would generally inspect the structure for the effects of microcracking or thermal damage. Advantageously, the ultrasonic inspection system is generally capable of injecting the ultrasonic signals into the structure and receiving the backscattered signals from the structure, even in instances in which the surface of the structure that faces the ultrasonic inspection apparatus has been primed, painted or includes lightening strike protection. Moreover, by utilizing a two-dimensional sensor array 12, the inspection system can inspect larger portions of a structure in an efficient and rapid manner.

Many modifications and other embodiments will come to mind to one skilled in the art to which the disclosure pertains having the benefit of the teachings presented in the foregoing descriptions and the associated drawings. For example, the array controller 14 and the computing device 16 have been depicted as separate elements. Alternatively, the computing device and the array controller may be embodied by the same device. Additionally, while ultrasonic transducers 18 have been described by both transmit and receive ultrasonic signals, the ultrasonic transducers may be comprised of distinct ultrasonic transmitters and ultrasonic transducers in other embodiments. Therefore, it is to be understood that the disclosure is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A system comprising:
    a two-dimensional array of ultrasonic transducers configured to be disposed upon a surface of a structure; and
    an array controller configured to trigger at least one a first array of emitting ultrasonic transducers to emit an ultrasonic signal into the structure, the array controller also configured to receive data representative of back scattered signals preferentially received by at least one a second array of receiving ultrasonic transducers from a portion of the structure offset from the at least one first array of emitting ultrasonic transducers that was triggered to emit the ultrasonic signal, the first array of emitting ultrasonic transducers and the second array of receiving ultrasonic transducers extending in different directions.

2. A system according to claim 1 wherein the two-dimensional array of ultrasonic transducers comprises a plurality of the first array of emitting ultrasonic transducers are positioned to emit ultrasonic signals that propagate along a predefined axis of propagation that intersects the surface of the structure at a non-orthogonal angle.

3. A system according to claim 1 wherein the first array of emitting ultrasonic transducers comprises a first linear array of ultrasonic transducers and the second array of receiving ultrasonic transducers comprise at least one second linear array of ultrasonic transducers, wherein one of the at least one first and second linear arrays of ultrasonic transducers comprises a linear array of ultrasonic transducers extending in a first direction, and wherein the other of the at least one first and second linear arrays of ultrasonic transducers comprises at least a pair of the linear arrays of ultrasonic transducers extending in different directions relative to one another.

4. A system according to claim 3 wherein the at least one first linear array of ultrasonic transducers comprises at least a pair of linear arrays extending in one direction and at least a pair of linear arrays extending in a different direction, wherein the pairs of linear arrays bound at least one ultrasonic transducer of the two-dimensional array, and wherein the at least one second linear array of ultrasonic transducers extends through the at least one ultrasonic transducer that is bounded by the pairs of linear arrays.

5. A system according to claim 3 wherein the at least one second linear array of ultrasonic transducers comprises at least a pair of linear arrays extending in one direction and at least a pair of linear arrays extending in a different direction, wherein the pairs of linear arrays bound at least one ultrasonic transducer of the two-dimensional array, and wherein the at least one first linear array of ultrasonic transducers extends through the at least one ultrasonic transducer that is bounded by the pairs of linear arrays.

6. A system comprising:
    an array controller configured to trigger at least one a first array of emitting ultrasonic transducers to emit ultrasonic signals into a structure, the array controller also configured to receive data representative of backscattered signals received by a plurality second array of receiving ultrasonic transducers from a portion of the structure offset from the first array of emitting ultrasonic transducers, the first array of emitting ultrasonic transducers and the second array of receiving ultrasonic transducers extending in different directions.

7. A system according to claim 6 wherein the first array of emitting ultrasonic transducers comprises a first linear array of ultrasonic transducers and the second array of receiving ultrasonic transducers comprise at least one second linear array of ultrasonic transducers, wherein one of the at least one first and second linear arrays of ultrasonic transducers comprises a linear array of ultrasonic transducers extending in a first direction, and wherein the other of the at least one first and second linear arrays of ultrasonic transducers comprises at least a pair of the linear arrays of ultrasonic transducers extending in different directions relative to one another.

8. A system according to claim 7 wherein the at least one first linear array of ultrasonic transducers comprises at least a pair of linear arrays extending in one direction and at least a pair of linear arrays extending in a different direction.

9. A system according to claim 8 wherein the at least one second linear array of ultrasonic transducers extends between at least one pair of the first linear arrays.

10. A system according to claim 8 wherein the pairs of linear arrays bound at least one ultrasonic transducer, and wherein the at least one second linear array of ultrasonic transducers extends through the at least one ultrasonic transducer that is bounded by the pairs of linear arrays.

11. A system according to claim 10 wherein the at least one first linear array of ultrasonic transducers extends between at least one pair of the second linear arrays.

12. A system according to claim 10 wherein the pairs of linear arrays bound at least one ultrasonic transducer, and wherein the at least one first linear array of ultrasonic transducers extends through the at least one ultrasonic transducer that is bounded by the pairs of linear arrays.

13. A system according to claim 7 wherein the at least one second linear array of ultrasonic transducers comprises at least a pair of linear arrays extending in one direction and at least a pair of linear arrays extending in a different direction.

14. A method comprising:
    triggering at least one a first array of emitting ultrasonic transducers to emit ultrasonic signals into a structure;
    receiving data representative of backscattered signals received by a plurality second array of receiving ultrasonic transducers from a portion of the structure offset from the first array of emitting ultrasonic transducers, the first array of emitting ultrasonic transducers and the second array of receiving ultrasonic transducers extending in different directions; and
    determining a material property of that portion of the structure associated with the emitting ultrasonic transducer based upon the data representative of the backscattered signals received by the plurality of receiving ultrasonic transducers.

15. A method according to claim 14 wherein the first array of emitting ultrasonic transducers comprises a first linear array of ultrasonic transducers and the second array of receiving ultrasonic transducers comprise at least one second linear array of ultrasonic transducers, wherein one of the at least one first and second linear arrays of ultrasonic transducers comprises a linear array of ultrasonic transducers extending in a first direction, and wherein the other of the at least one first and second linear arrays of ultrasonic transducers comprises at least a pair of the linear arrays of ultrasonic transducers extending in different directions relative to one another.

16. A method according to claim 15 wherein the at least one first linear array of ultrasonic transducers comprises at least a pair of linear arrays extending in one direction and at least a pair of linear arrays extending in a different direction.

17. A method according to claim 15 wherein the at least one second linear array of ultrasonic transducers comprises at least a pair of linear arrays extending in one direction and at least a pair of linear arrays extending in a different direction.

* * * * *